United States Patent
Tsai

(10) Patent No.: US 9,501,625 B2
(45) Date of Patent: Nov. 22, 2016

(54) ASSISTANCE SYSTEM AND METHOD FOR TAKING MEDICINE

(71) Applicant: NATIONAL CHENG KUNG UNIVERSITY, Tainan (TW)

(72) Inventor: Pei-Hsuan Tsai, Taipei (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 446 days.

(21) Appl. No.: 13/837,780

(22) Filed: Mar. 15, 2013

(65) Prior Publication Data
US 2014/0074496 A1    Mar. 13, 2014

(30) Foreign Application Priority Data
Sep. 10, 2012    (TW) .............................. 101132957 A

(51) Int. Cl.
*G06F 19/00* (2011.01)
(52) U.S. Cl.
CPC ................................. *G06F 19/3462* (2013.01)
(58) Field of Classification Search
USPC ................................. 235/435, 439, 454, 462
See application file for complete search history.

(56) References Cited

U.S. PATENT DOCUMENTS

| 5,774,865 A * | 6/1998 | Glynn ................................ 705/2 |
| 6,294,999 B1 * | 9/2001 | Yarin et al. ................. 340/573.1 |
| 2011/0015945 A1 * | 1/2011 | Addy ................... G06F 19/3462 705/3 |
| 2012/0083666 A1 * | 4/2012 | Waugh .................. A61J 7/0084 600/300 |

FOREIGN PATENT DOCUMENTS

| TW | 255027 | 8/1995 |
| TW | 574662 B | 2/2004 |
| TW | I286706 B | 9/2007 |
| TW | 200939727 A | 9/2009 |

* cited by examiner

*Primary Examiner* — Matthew Mikels
(74) *Attorney, Agent, or Firm* — Muncy, Geissler, Olds & Lowe PC

(57) ABSTRACT

An assistance system for taking medicine includes at least a pill container, a processing module and an image capturing module. The pill container is for containing a first medicine and has a first barcode corresponding to the first medicine. The image capturing module is coupled to the processing module and for capturing an image having the first barcode. The processing module assists a person (patient) to take medicine according to information of the first barcode.

16 Claims, 7 Drawing Sheets

---

S10 — containing a first medicine in at least a pill container, which has a first barcode corresponding to the first medicine S20 — capturing an image, having the first barcode, through an image capturing module S30 — assisting the person to take medicine according to data of the first barcode through a processing module

ASSISTANCE SYSTEM AND METHOD FOR TAKING MEDICINE

CROSS REFERENCE TO RELATED APPLICATIONS

This Non-provisional application claims priority under 35 U.S.C. §119(a) on Patent Application No(s). 101132957 filed in Taiwan, Republic of China on Sep. 10, 2012, the entire contents of which are hereby incorporated by reference.

BACKGROUND OF THE INVENTION

1. Field of Invention

The invention relates to an assistance system and method for taking medicine.

2. Related Art

The advancement of technology improves the people's life and diet, but makes the modem human beings be much troubled by the diseases of civilization, such as chronic diseases including the hypertension, cancer, cardiovascular disease, diabetes or the like; or mental illnesses including the depressive illness, bipolar disorder or the like. The treatments for these diseases need to rely on the long-term medicine treatment. Although the technology has getting more and more advanced than the prior art and the digitized era has come, the conditions of medication errors still come out one after the other.

At present, a complete administration and medicine assisting system has not been available. In the current hospital administration condition, after the patient goes to the hospital or clinic for the consultation, the patient receives several days of medicines, which are usually mixed and placed in a medicine bag, and the hospital or clinic staff records the medication information, such as the time interval and the number of the medications, on the medicine bag. The patient has to take the medicines from the medicine bag according to the doctor's advice. However, the busy office workers or old persons tend to forget to take the medicine. In addition, there is an extremely high medication risk when the medicine kinds and the medication dosages are diversified.

In addition, the information associated with the medicine involves the high professional knowledge. When the information recorded on the prescription is simple and incomplete and no detailed manual is provided, the patient has to perform the search from the network or books if he or she wants to know the information associated with the medicine. This is quite inconvenient. More particularly, upon medication, the real-time reference information cannot be obtained, and whether the medication is correct cannot be clearly obtained. Thus, it is further difficult to reduce the risk of medication error.

Generally speaking, as long as the medicines are dispensed through the non-professional, either the family member, the caretaker or the patient, after the medicines are taken from the hospital and before the medicines are taken, there is a considerable risk of causing the condition of medication error. The existing art also does not have the better solution for the current and mostly frequently seen medication errors, including taking the incorrect medicine, taking the medicine at the incorrect time, forgetting the kinds of the medicines to be taken, and the like.

Thus, how to provide an assistance system and an assistance method for taking the medicine to decrease the medicine taking problems, which are caused by the non-professional participating in the process after the medicine is received and before the medicine is taken, has become an important subject. The system and method can assist the patient to take the medicine as if under the monitoring and consulting of the professional to solve the medicine taking problems caused by the patient who does not follow the doctor's advice. The system and method can further precisely provide the medication reference information (or even the patient's medical history data), record the patient's medication condition, and remind the patient to take the medicine or remind the patient of the doctor's advice at the suitable time point, thereby reducing the too-high medication error rate.

SUMMARY OF THE INVENTION

In view of the foregoing, an objective of the invention is to provide an assistance system and an assistance method for taking medicine, which can precisely provide the information associated with the medication, such as the medicine taking information, the medicine information and the like, and can solve the conventional problems that the reference information cannot be obtained upon medication and that whether the medication is correct cannot be obtained, thereby effectively reducing the medication error rate.

Another objective of the invention is to provide an assistance system and an assistance method for taking medicine, which can remind the patient to take the medicine or remind the patient of the doctor's advice at the suitable time point, thereby reducing the condition that the medicine is taken at the incorrect time, that the patient forgets to take the medicine, or that the medication error occurs.

To achieve the above objectives, the present invention discloses an assistance system for taking medicine. The system comprises at least a pill container, a processing module and an image capturing module. The pill container is for containing a first medicine and has a first barcode corresponding to the first medicine. The image capturing module is coupled to the processing module and captures an image having the first barcode. The processing module assists a person (patient) to take medicine according to data of the first barcode.

The present invention also discloses a method for assisting a person to take medicine, the method comprising the steps of containing a first medicine in at least a pill container, which has a first barcode corresponding to the first medicine; capturing an image, having the first barcode, through an image capturing module; and assisting the person to take medicine according to data of the first barcode through a processing module.

In one embodiment of the invention, the processing module is disposed in an electronic medicine box or a handheld electronic device.

In one embodiment of the invention, the electronic medicine box or the handheld electronic device controls the pill container to open at a time point or to output a reminding signal at a time point according to a signal outputted from the processing module.

In one embodiment of the invention, the system further comprises an electronic medicine box having a plurality of positioning patterns, and the processing module reads the data of the first barcode of the image through the positioning patterns.

In one embodiment of the invention, the processing module reads the data of the first barcode of the image through the positioning patterns by defining a read range in the image according to the positioning patterns, dividing the read range into a plurality of read blocks, locating the first barcode in one of the read blocks, and reading the first barcode in the read block.

In one embodiment of the invention, the system comprises two pill containers, while one of the pill containers contains the first medicine, and the other pill container contains a second medicine different from the first medicine.

In one embodiment of the invention, the system further comprises a data transfer module, which is coupled to the processing module and signally connected to a remote server.

In one embodiment of the invention, the remote server reads the data of the first barcode, and returns the processing module through the data transfer module to assist the person to take medicine.

In one embodiment of the invention, the remote server has a data storage module which stores barcode data.

In one embodiment of the invention, the remote server receives read data, outputted from the processing module according to the data of the first barcode, compares the read data with the barcode data of the data storage module, and converts the read data into assistance medication data returned to the processing module.

In one embodiment of the invention, the first barcode is disposed on the pill container before or after the pill container contains the first medicine by way of printing, adhering or engraving.

According to the assistance system and method of the invention for taking medicine, the pill container has the barcode. When being used in conjunction with the processing module and the image capturing module, the information of the barcode can be read to reproduce the medicine taking information, the medicine information, the personal identification and the like. Even if the patient takes the medicine in a non-professional place, such as the house or the nursing center, the medicine is taken as if under the professional's monitoring and consulting. What is important is that because the barcode serves as the medium for carrying the information, it can record more contents, is suitable for the digitization and electrization applications, and does not rely on the memory of the patient or the family member, thereby avoiding the problems of oblivion or incorrect interpretation. Thus, the invention is advantageous to the domination of the medicine taking information and the medicine information, for example, and can further avoid the condition of the medication error by again checking the personal identification information.

What is more important is that because the pill container is configured such that the medicines are filled and the barcodes are recorded under the monitoring of the professional at the medical institution or the pharmaceutical factory, for example, it is possible to obtain what the packaged medicine is and how to take medicine using the processing module and the image capturing module to directly read the recorded contents of the barcodes, thereby implementing the safe medicine taking mode of guiding the person to take medicine using the automation control means. Thus, the conventional operation mode, in which the non-professional (e.g. the patient, the family member or the caretaker) takes the medicine out and places the medicine into the medicine box based on the memory; can be decreased or avoided in the nursing caretaker or the self care duration, thereby reducing the potential risk and effectively decreasing the medication error rate.

Compared with the typical medicine box, which only marks the week and time, or the electronic medicine box with the reminding function, the invention provides a perfect assistance system for taking medicine through the module which integrates the pill container, the barcode and the readable barcode together. More particularly, the medication can be precisely managed and reminded without setting even if the prescription contents are different or the medication instructions are changed.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1:
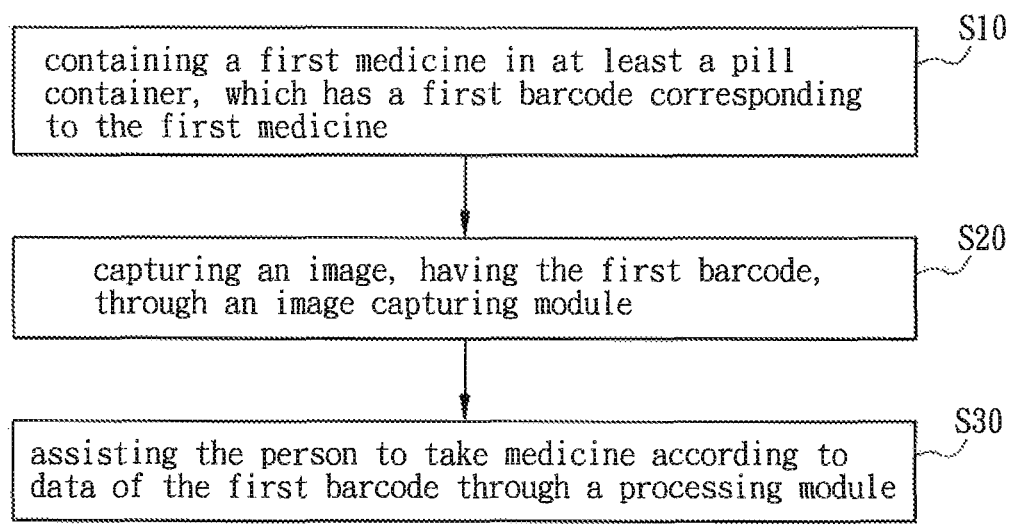
FIG. 1 is a flow chart showing steps of an assistance method for taking medicine according to a preferred embodiment of the invention.

FIG. 1 is a flow chart showing steps of an assistance method for taking medicine according to a preferred embodiment of the invention. Referring to FIG. 1, the method for assisting a person (patient) to take medicine includes the following steps. In step S10, a first medicine is contained in at least a pill container having a first barcode corresponding to the first medicine. In step S20, an image having the first barcode is captured through an image capturing module. In step S30, a processing module assists the person to take medicine according to the data of the first barcode.

Figure 2A:
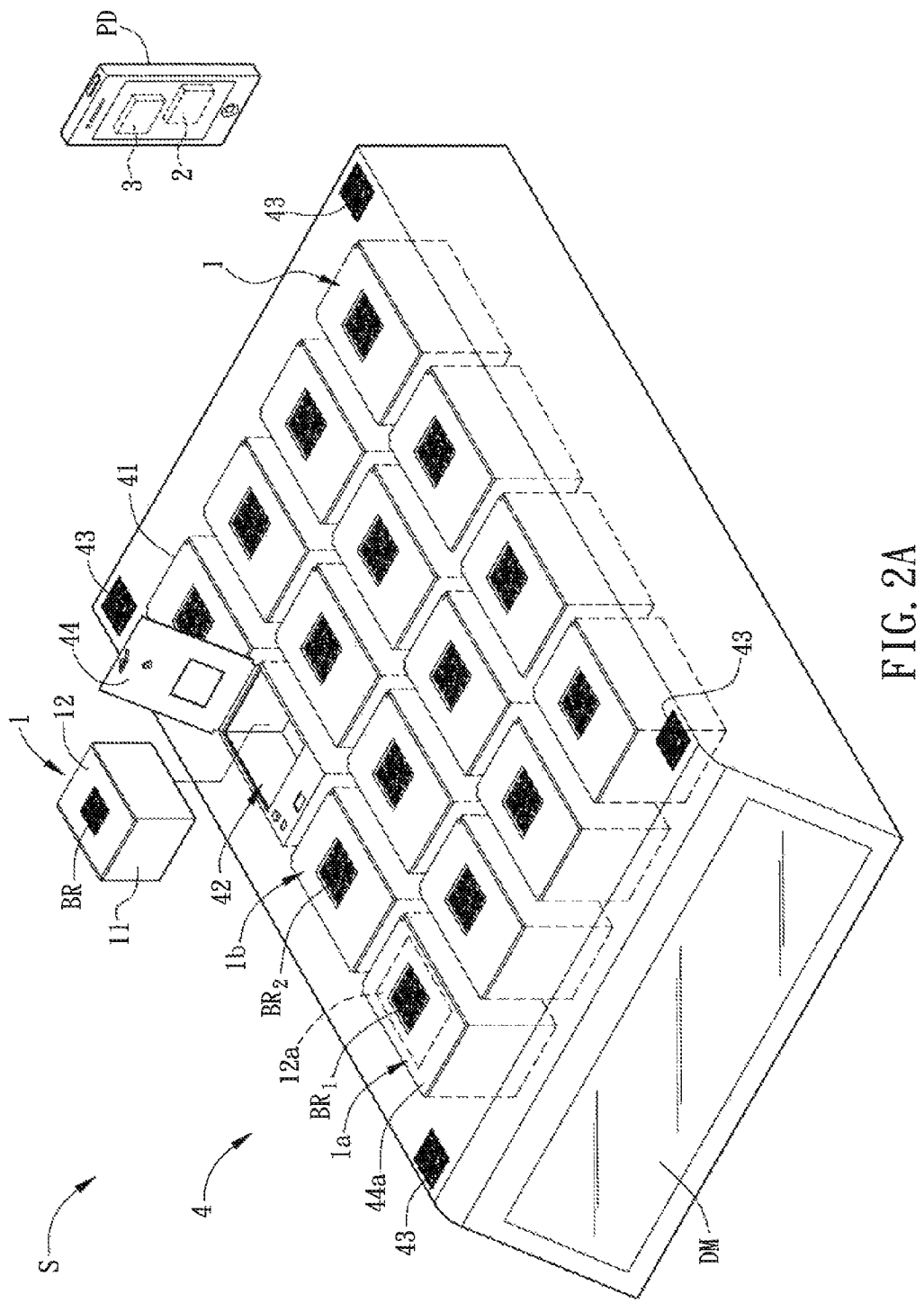
FIG. 2A is a partially perspective schematic illustration showing a system for implementing the method of FIG. 1.

In this embodiment, the method may be implemented by an assistance system for taking medicine, wherein the system includes at least a pill container, a processing module and an image capturing module. FIG. 2A is a partially perspective schematic illustration showing a system for implementing the method of FIG. 1. Referring to FIG. 2A, the system S includes a plurality of pill containers 1, a processing module 2 and an image capturing module 3. The system S may mainly include an electronic medicine box 4 and a portable or handheld electronic device PD, which may be a smart mobile phone or a tablet computer. The processing module 2 and the image capturing module 3 are disposed in the handheld electronic device PD, and the handheld electronic device PD is coupled to the electronic medicine box 4 in a wireless connection manner. Of course, in other embodiments, the pill container may also be similar to the conventional medicine box, so that the corresponding device can execute the processing and computing functions.

However, it is to be specified that the system applying the method of the invention is not restricted to a particular configuration. The configuration shown in FIG. 2A is only for the illustrative but non-restrictive purpose. Specifically, in other embodiments, the system may have more than one pill container, such as two, four, eight, twelve containers. Alternatively, the image capturing module and the processing module may also be disposed in the electronic medicine box, which independently operates the main function. Alternatively, the processing module and the image capturing module may also be disposed in the electronic medicine box and the handheld electronic device, respectively, and are coupled together in a wired or wireless manner to implement the integrated effect.

Figure 2B:
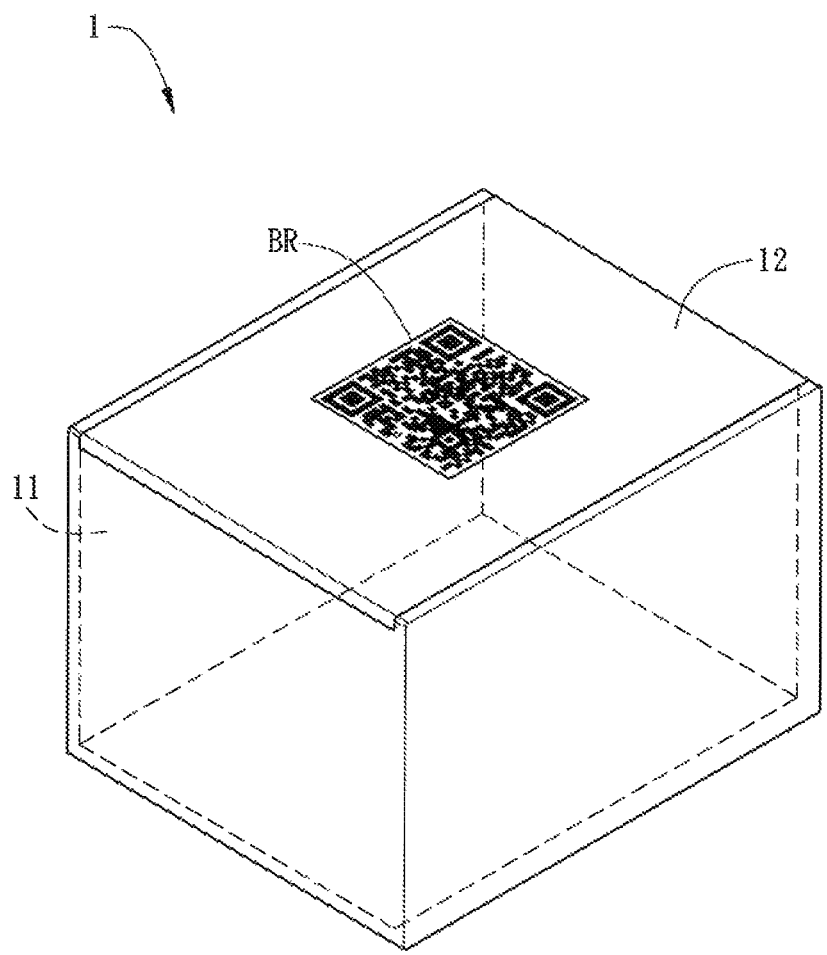
FIG. 2B is a perspective schematic illustration showing a pill container of the system of FIG. 2A.

The system S includes sixteen pill containers 1, which are the same. FIG. 2B is a perspective schematic illustration showing a pill container of the system of FIG. 2A. As shown in FIG. 2B, the pill container 1 is a cuboid and has a containing space 11 and a movable upper cover portion 12, which can be opened and closed. In this embodiment, the pill container 1 is integrally formed. Of course, in other embodiments, the containing space may also make the upper cover portion be able to open and close through a pivot.

Illustrations will be continued by taking two pill containers 1a and 1b as examples (see FIG. 2A). The pill container 1a contains the first medicine, and the pill container 1b contains a second medicine. The first medicine and the second medicine pertain to different kinds of medicines, and have different medication ways and medication instructions. Therefore, the pill container 1a corresponds to the first medicine and has a first barcode $BR_1$, while the pill container 1b corresponds to the second medicine and has a second barcode $BR_2$, wherein the barcodes can be read and identified. The first barcode $BR_1$ or the second barcode $BR_2$ may be disposed on the pill container 1a or 1b by way of printing, adhering or engraving before or after the pill container 1a or 1b contains the first or second medicine.

Either the pill container 1a or 1b contains the first barcode $BR_1$ or the second barcode $BR_2$ according to different medicines contained therein, or the pill container 1a or 1b contains different medicines according to the first barcode $BR_1$ or the second barcode $BR_2$ disposed thereon, the correct corresponding relationship can be ensured under the monitoring of the professional. Thus, the information associated with various medicines can be transferred out correctly without through the non-professional, such as the patient, the family member or the caretaker.

The information associated with the medicine includes, for example, the medicine taking information, the medicine property, the medicine information, the personal information of the patient, or the like. The medicine taking information may contain the information, such as the medication time, the medication frequency, the dosage, the taking way, the precaution or the like. The medicine information may include the information, such as the medicine exterior model, the medicine name, the preservation way, the after-affect or the like. The personal identification information includes the information, such as the name and surname, the medical record number code, the medicine allergy or back to clinic arrangement.

Taking the pill container 1a as an example, the data, which is an arbitrary combination of the above-mentioned information, can be processed into the first barcode $BR_1$ through a barcode editing program, and then the first barcode $BR_1$ is disposed on the upper cover portion 12a of the pill container 1a.

When the first medicine has a wide applicability, the first medicine is directly packaged by the pill container 1a, and the associated information is directly recorded on the pill container 1a through the barcode $BR_1$ during the pharmaceutical processes in the pharmaceutical factory. However, it is practical to have the health care worker package the first medicine into the pill container 1a while recording the data on the pill container 1a through the first barcode $BR_1$ according to the doctor's advice after the patient has seen the doctor. However, no matter which method is used, the trouble of having to write or output the medicine memo in each administration can be eliminated. On the one hand, the medical manpower can be saved. On the other hand, the information can be digitized so that the information can be provided to a person (patient), who needs to take medicine, in a more suitable manner.

Referring to FIG. 2A, the electronic medicine box 4 has a plurality of housing units 41 each providing a containing space 42 and having a cover 44, so that the pill containers 1 can be detachably contained in the housing units 41, respectively. After the pill container 1a is disposed in the electronic medicine box 4, the first barcode $BR_1$ still can be exposed and in a readable state. Of course, in other embodiments, a plurality of pill containers 1 can be merged into one unit, such as the available unit having the structure similar to that with one row or one set of conventional medicine boxes. Regardless of the pill container model, it is preferred that all the barcodes can be concurrently captured when the barcodes are read.

Figure 3A:
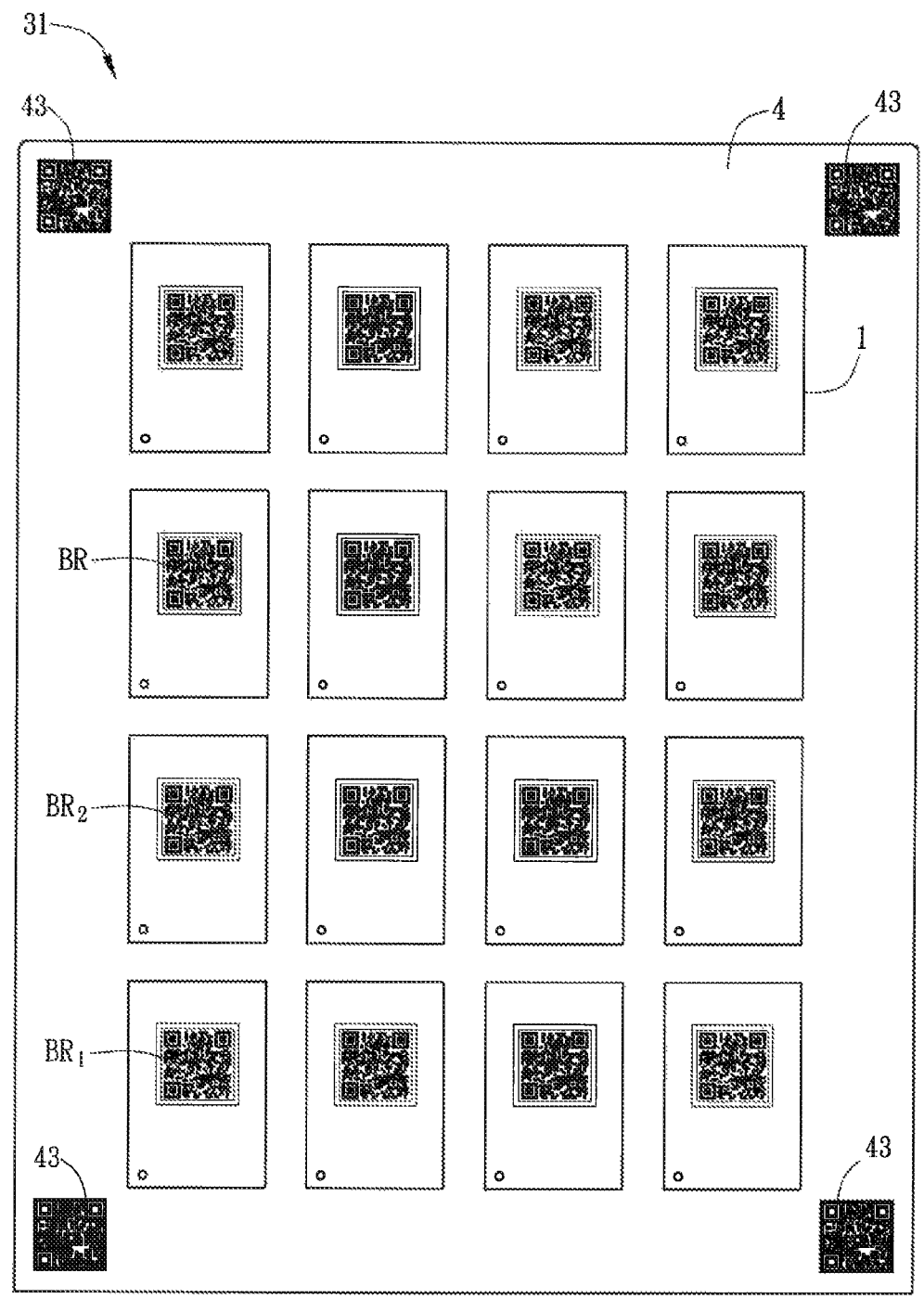
FIG. 3A is a schematic illustration showing an image of an electronic medicine box of FIG. 2A combined with a pill container, wherein the image is captured by an image capturing module at a top-view angle.

In the step S20, an image 31 is captured through the image capturing module 3 of the handheld electronic device PD. FIG. 3A is a schematic illustration showing an image of the electronic medicine box of FIG. 2A combined with the pill container, wherein the image is captured by the image capturing module at a top-view angle. Referring to FIGS. 2A and 3A concurrently, the image 31 has a plurality of barcodes BR including the first barcode $BR_1$ and the second barcode $BR_2$.

In the step S30, the processing module 2 assists a person (patient) to take medicine according to the data of the barcode BR. In this embodiment, the image 31 captured by the image capturing module 3 of the handheld electronic device PD may have a plurality of positioning patterns 43, such as four positioning patterns 43 shown in the drawing. The processing module 2 can read the data of the barcode BR in the image 31 through the positioning patterns 43.

The four positioning patterns 43 are disposed on the electronic medicine box 4, and are disposed at four corners of the upper surface of the housing of the electronic medicine box 4, respectively, and neighbor the exposed barcode BR. Thus, when the handheld electronic device PD is used, the above-mentioned image 31 can be obtained at the top-view angle when photographing the electronic medicine box 4 from top to bottom.

In addition, it is to be noted that the positioning pattern 43 of this embodiment may be a two-dimensional barcode, which can be read using the existing two-dimensional barcode library recognition technique, has the effect of simplifying the calculation complexity and is advantageous to the combination with the existing technique.

Figure 3B:
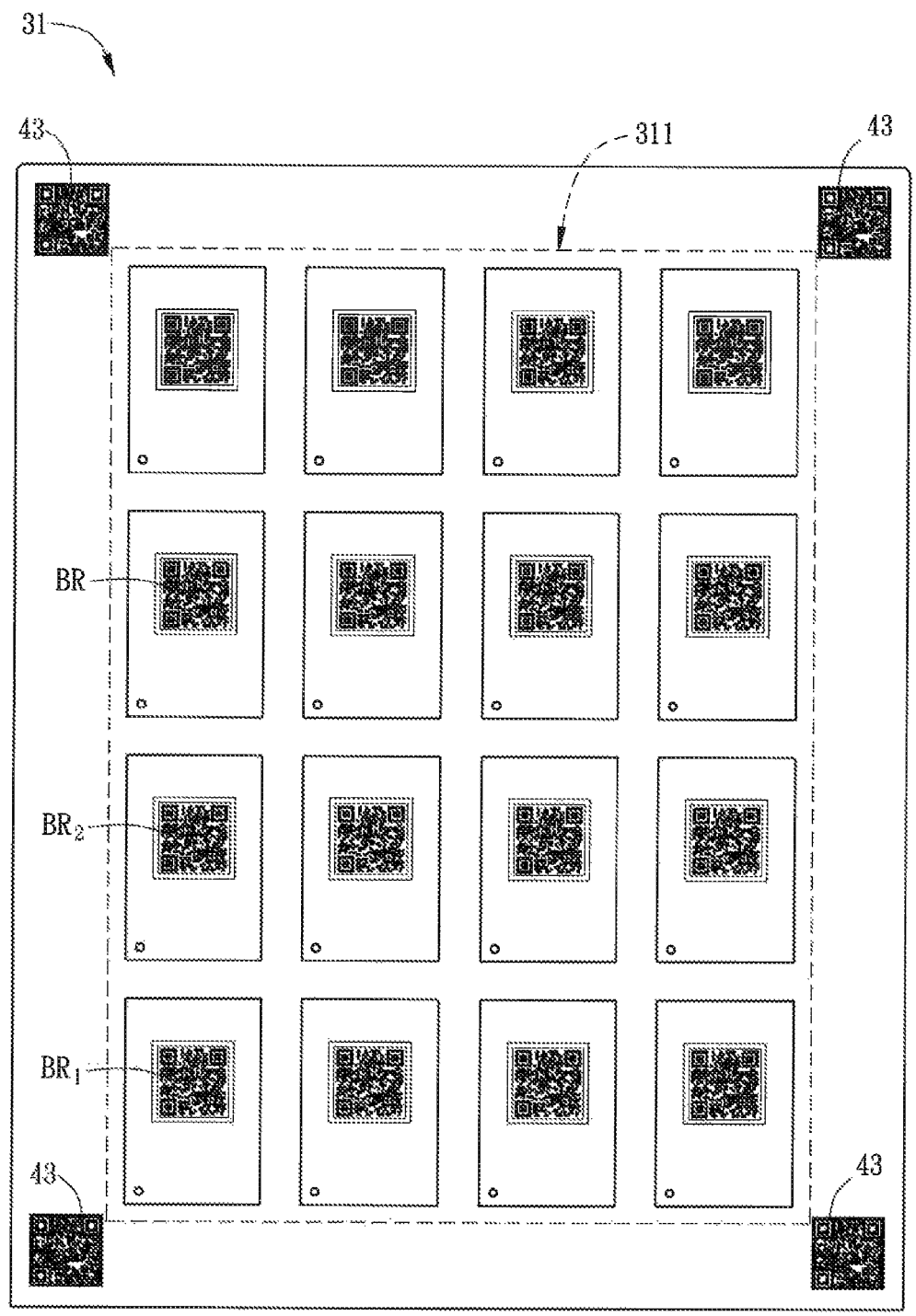
FIG. 3B is a schematic illustration showing the image of FIG. 3A in a defined read range.

FIG. 3B is a schematic illustration showing the image of FIG. 3A in a defined read range. Referring to FIGS. 2A and 3B concurrently, after the image 31 is acquired, the processing module 2 can firstly divide the image 31 into four portions according to a specific algorithm, for example, and then recognize two neighboring pixels with the greater difference of contrast among the four image blocks, and thus find the boundary of the positioning pattern 43. Thereafter, four corners on the boundary of the positioning pattern 43 are marked. Then, four innermost corners of the four positioning patterns 43 are connected together in straight lines, respectively, to define a frame range as the read range 311. It is to be noted that the read range 311 does not contain four positioning patterns 43. Of course, in other embodiments, three, six or eight positioning patterns may also be used based on the same principle in order to define the range more precisely in conjunction with different shapes of read ranges. Alternatively, other arbitrary points of the positioning patterns are connected to form the frame range, but the invention is not particularly restricted thereto.

Figure 3C:
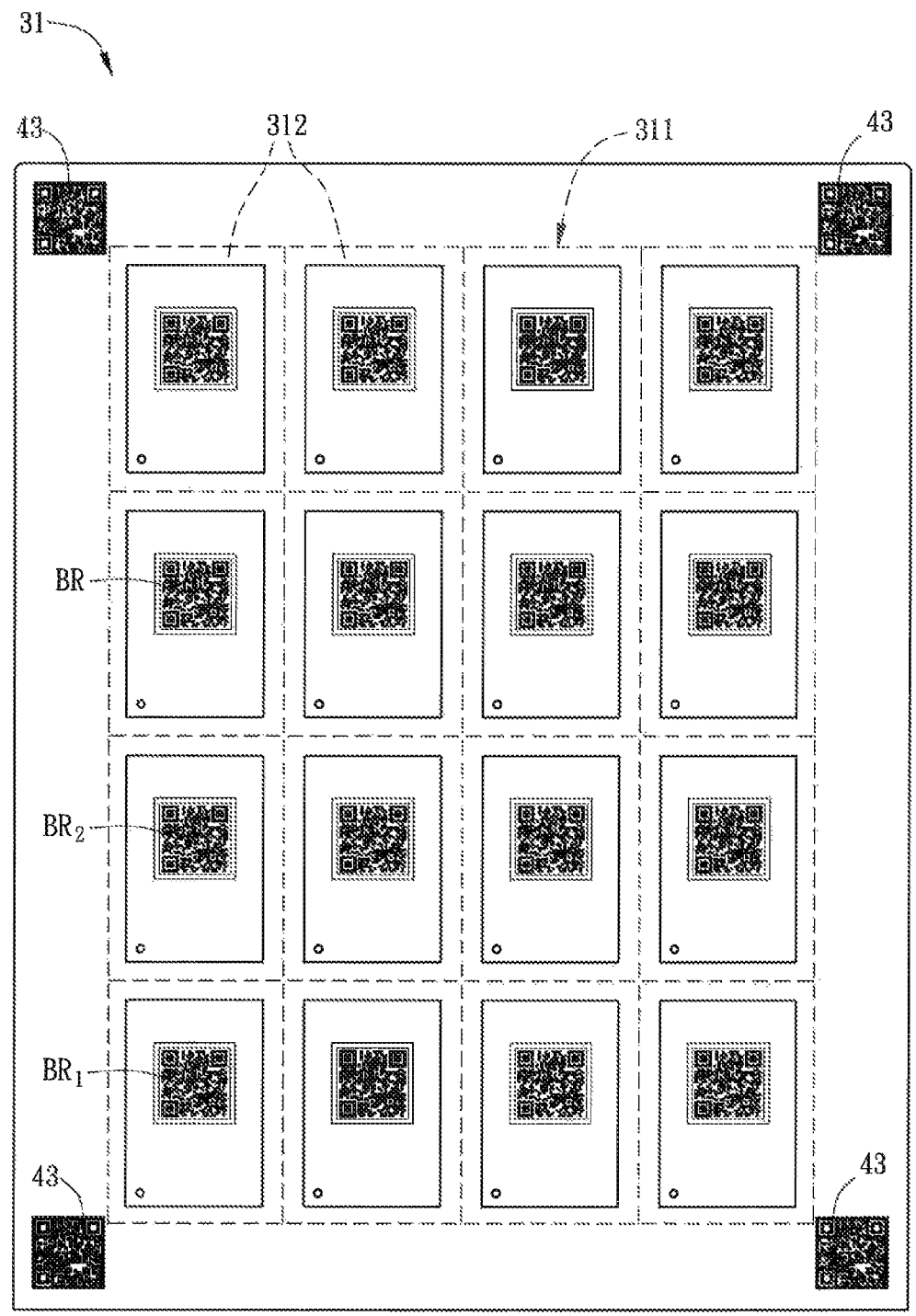
FIG. 3C is a schematic illustration showing the read range of FIG. 3B divided into a plurality of read blocks.

FIG. 3C is a schematic illustration showing the read range of FIG. 3B divided into a plurality of read blocks. Referring to FIGS. 2A and 3C concurrently, the processing module 2 then divides the read range 311 into a plurality of read blocks 312 so that each barcode BR is disposed in one of the read blocks 312. The medicine box containers 1 have substantially the same size and are placed at the positions of the electronic medicine box 4 with a predetermined regularity. So, in the actual implementation, it is possible to perform the dividing through an algorithm directly according to the size of the upper cover of the pill container 1 and a predetermined array value, for example, by means of the vertical axes and the horizontal axes interlacing with each other, so that the read range 311 is divided into sixteen read blocks 312, as shown in the drawing.

After the read block 312 has been completely defined, the original barcodes BR in the image 3 are disposed in the read blocks 312 with the same size and shape, respectively. Next, the processing module 2 reads the barcodes BR in the read blocks 312 one by one from the first barcode $BR_1$, for example, using the library, so that multiple barcodes BR can be recognized at a time.

According to the above-mentioned steps, it is possible to achieve the effects of speeding up the operation procedure so that the electronic medicine box or the handheld electronic device can perform the large-range barcode reading and achieve the effect of saving the labor loss. In addition, it is possible to avoid the process of reading of one barcode at a time, in which the barcodes must be read according to the specific order set by the typical processing module and the potential risk of operation errors is caused. In addition, most important of all, the reading of the barcode and the data input after reading do not relate to the order or the position, so the patient, the caretaker or the family member can arbitrarily place the pill container without worrying about the medication error risk caused by relying on the memory to dispense the medicines.

As mentioned hereinabove, the technology of using the library to recognize the positioning pattern with the barcode pattern and to recognize the barcode are well known in the art, so detailed descriptions thereof will be omitted.

Also, in one aspect of the above-mentioned embodiment, the process of reading the barcode may further include the following steps of enhancing the readability of the barcode in the image, highlighting the positioning pattern or providing another image again when the reading of any barcode fails. The readability of the barcode in the image is enhanced to prevent the interference present in the image or the image capturing error from causing the recognition stoppage, so that the recognizable extent of the image can be enhanced. The implementation means include a contrast enhancing procedure, a color calibrating procedure, a keystone calibrating procedure or a noise eliminating procedure.

The process of highlighting the positioning pattern may, for example, convert the positioning pattern in the image into the highlighted barcode, so that the difference between the highlighted barcode and the barcode on the pill container becomes more significant, and the position of the positioning pattern can be recognized more precisely. If the reading of any barcode fails, another image is provided again to avoid the miss that any information is not extracted, and this is an automatic feedback control mechanism.

After the information recorded by each barcode BR, including the first barcode $BR_1$, the processing module 2 can assist a person (patient) to take medicine according to the data of the barcode BR. Of course, it is to be firstly specified that the process of assisting the person to take medicine in this invention is not particularly restricted to any proceeding manner, and may include the process of directly providing the medicine taking information to the person, or providing the information to the caretaker or the family member to indirectly assist the person to take medicine. In addition, the specific content of assistance may include displaying the medication instruction or the doctor's advice, reminding the person of the medication at the correct time, displaying the medicine information, verifying the personal data or the like. In the following, several representative examples will be described. However, other examples satisfying the same or similar concepts should be deemed as falling within the scope of the invention.

As shown in FIG. 2A, for example, the processing module 2 of the handheld electronic device PD can output a control signal at the medication time, recorded by the first barcode $BR_1$, to control a cover 44a of the electronic medicine box 4, and to open the upper cover portion 12a in a linking-up manner as the means of reminding the person of the medication through the mutual magnetic attraction between the cover 44a and the upper cover portion 12a of the pill container 1a. Also, each housing unit 41 may be equipped with a warning element, such as an indicator or the like. Alternatively, the electronic medicine box 4 may be equipped with a buzzer for providing the reminding effect similarly. It is to be noted that the electronic medicine box may also transmit the reminding signal to the handheld electronic device to remind the person to take medicine in the embodiment where the processing module is disposed in the electronic medicine box.

In addition, while reminding the medication, it is also possible to display the data, such as the medication instruction, the personal identification information, the medicine security information or the like, on a display module DM of the electronic medicine box 4, and thus to implement the concept of simulating the medication under the monitoring or consulting of the professional.

Figure 4A:
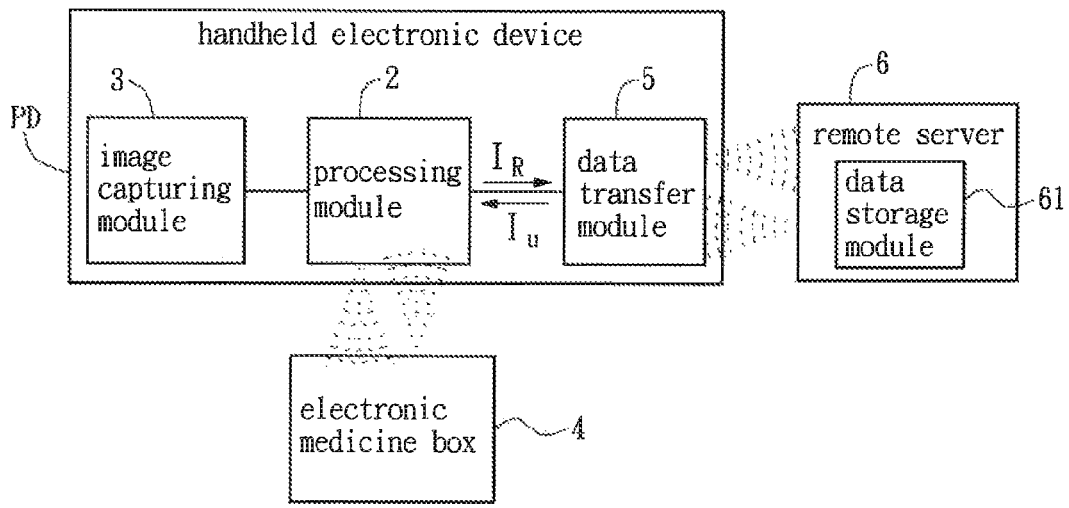
FIG. 4A is a block diagram showing a system, which is adapted to the implementation of the method of the invention according to another preferred embodiment.

FIG. 4A is a block diagram showing a system, which is adapted to the implementation of the method of the invention according to another preferred embodiment. As shown in FIG. 4A, the medicine taking assistance system implementing the method of the invention is substantially the same as that mentioned hereinabove, but further includes a data transfer module 5, which is disposed in the handheld electronic device PD and coupled to the processing module 2 through a wired connection. In addition, the data transfer module 5 may be signally connected to a remote server 6 in a wired or wireless manner. Of course, in other aspects, the data transfer module may also be disposed in the electronic medicine box or other electronic devices, and be coupled to the processing module through the wireless or wired connection according to the position of the processing module (either the handheld electronic device or the electronic medicine box).

The remote server 6 can read the data of the barcode, and return the data to the processing module 2 through the data transfer module 5 so that the processing module 2 assists the person to take medicine. In other words, the processing module 2 in this embodiment may further be simplified in the design, and the work of judging the data of the barcode is performed in the remote server 6, and this is advantageous to the expansion application and the light and thin product.

Figure 4B:
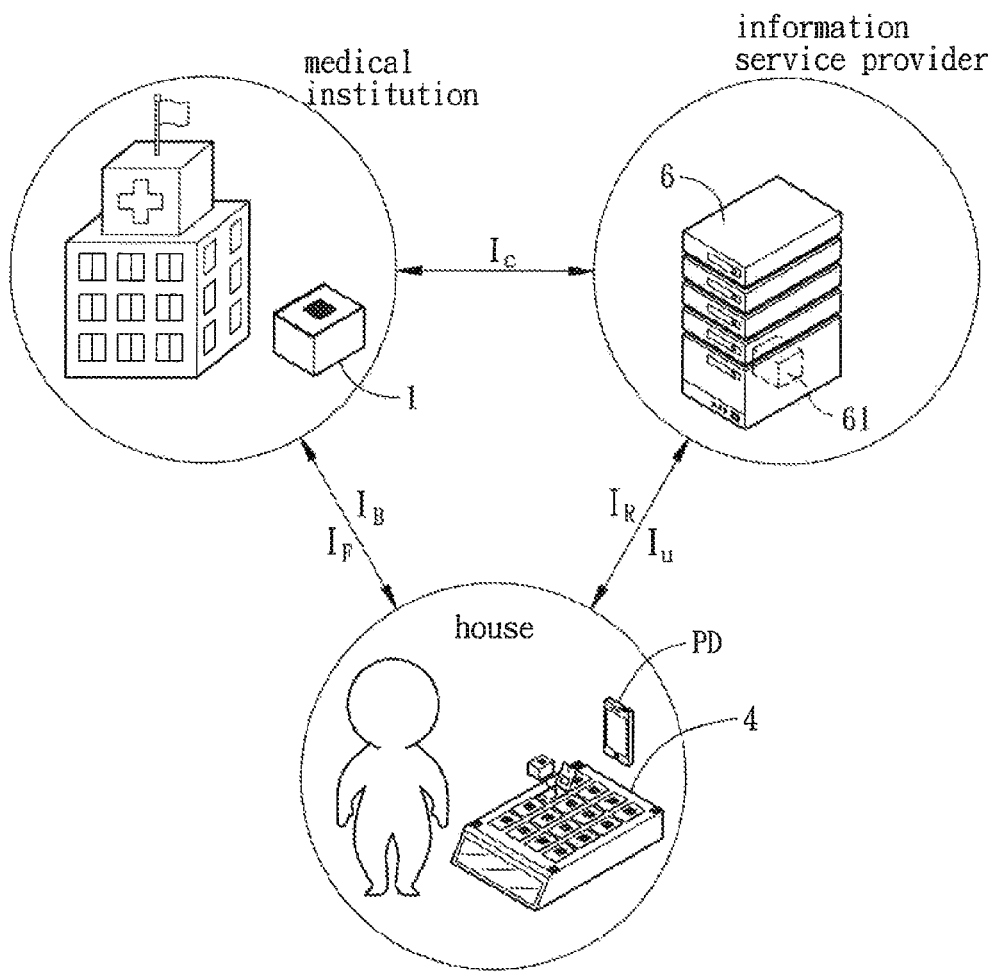
FIG. 4B is a schematic illustration showing a medical information platform constructed by the system of FIG. 4A.

FIG. 4B is a schematic illustration showing a medical information platform constructed by the system of FIG. 4A. Referring to FIGS. 4A and 4B concurrently, the remote server 6 has a data storage module 61, which stores reference data corresponding to the barcode data, the contents of which may include the medicine taking information, the medicine property, the medicine information or the patient's personal information, such as the patient's identification data and medical history, which have been mentioned in the above-mentioned embodiment. Specifically speaking, after the remote server 6 receives the read data $I_R$ outputted by the processing module 2 after reading the barcode, the remote server 6 compares the read data $I_R$ with the reference data in the data storage module 61. Then, the remote server 6 returns assistance medication data $I_U$, which is obtained after comparison, to the processing module 2, so that the electronic medicine box 4 or the handheld electronic device PD reminds the person to take medicine.

Of course, as mentioned hereinabove, the system and service associated with the medicine taking information can be implemented on the cloud based on this medical information platform. Specifically speaking, in addition to transferring the read data $I_R$ and the assistance medication data $I_U$, the medical institution can safely let the patient bring the important information, such as the medication instruction, through the barcode in the form of barcode data $I_B$, and the patient may also bring feedback data $I_F$, recorded on the electronic medicine box 4 or the handheld electronic device PD, back to the medical institution for reference. Also, the information service provider and the medical institution may also exchange the real-time update data $I_C$, including the new medicine, new knowledge or medication instruction, with each other, so that the information service content can be enhanced.

In addition, although the example barcode in the above-mentioned embodiment is a two-dimensional barcode, the barcode may also be a one-dimensional barcode in the practical application, and the invention is not particularly restricted thereto. Of course, the two-dimensional barcode does not intend to restrict the invention, and the quick response (QR) code, the PDF417 code or the like may also be adopted in this invention.

The invention additionally discloses an assistance system for taking medicine. Since the system is substantially the same as the system adapted to the implementation of the method of the invention, its technological contents and element components may be referred to those mentioned hereinabove, and detailed descriptions thereof will be omitted.

In summary, according to the assistance system and method of the invention for taking medicine, the pill container has the barcode. When being used in conjunction with the processing module and the image capturing module, the information of the barcode can be read to reproduce the medicine taking information, the medicine information, the personal identification and the like. Even if the patient takes the medicine in a non-professional place, such as the house or the nursing center, the medicine is taken as if under the professional's monitoring and consulting. What is important is that because the barcode serves as the medium for carrying the information, it can record more contents, is suitable for the digitization and electrization applications, and does not rely on the memory of the patient or the family member, thereby avoiding the problems of oblivion or incorrect interpretation. Thus, the invention is advantageous to the domination of the medicine taking information and the medicine information, for example, and can further avoid the condition of the medication error by again checking the personal identification information.

What is more important is that because the pill container is configured such that the medicines are filled and the barcodes are recorded under the monitoring of the professional at the medical institution or the pharmaceutical factory, for example, it is possible to obtain what the packaged medicine is and how to take medicine using the processing module and the image capturing module to directly read the recorded contents of the barcodes, thereby implementing the safe medicine taking mode of guiding the person to take medicine using the automation control means. Thus, the conventional operation mode, in which the non-professional (e.g. the patient, the family member or the caretaker) takes the medicine out and places the medicine into the medicine box based on the memory, can be decreased or avoided in the nursing caretaker or the self care duration, thereby reducing the potential risk and effectively decreasing the medication error rate.

Compared with the typical medicine box, which only marks the week and time, or the electronic medicine box with the reminding function, the invention provides a perfect assistance system for taking medicine through the module which integrates the pill container, the barcode and the readable barcode together. More particularly, the medication can be precisely managed and reminded without setting even if the prescription contents are different or the medication instructions are changed.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An assistance system for taking medicine, the system comprising:
    an electronic medicine box comprising:
        a base having a plurality of housing units; and
        a plurality of upper cover portions movably connected to the housing units, respectively, wherein a plurality of positioning patterns are disposed on the electronic medicine box;
    a plurality of pill containers detachably disposed in the housing units of the electronic medicine box respectively, wherein each of the pill containers comprises:
        an accommodating portion configured to contain a medicine; and
        a cover portion configured to be movably connected to the accommodating portion and to have a two-dimensional barcode corresponding to the medicine in the accommodating portion, wherein when the pill containers are disposed in the electronic medicine box, the two-dimensional barcodes are readable;

an image capturing module configured to capture an image having the two-dimensional barcodes and the positioning patterns; and a processing module coupled to the image capturing module and configured to perform the steps of:
generating a boundary of each of the positioning patterns;
marking four corners of the boundary of each of the positioning patterns;
connecting an innermost corner of each of the positioning patterns to define a reading area;
dividing the reading area into a plurality of reading blocks, each of the two-dimensional barcodes being positioned in one of the reading blockings respectively;
reading the two-dimensional barcodes in the reading blocks respectively; and
outputting an assisting signal to assist a person to take medicine according to the data of the two-dimensional barcode,
wherein the electronic medicine box or a handheld electronic device controls the pill container to open at a time point or to output a reminding signal at a time point according to the assisting signal.

2. The system according to claim 1, wherein the processing module is disposed in the electronic medicine box or the handheld electronic device.

3. The system according to claim 1, wherein at least two of the pill containers contain different medicine.

4. The system according to claim 1, further comprising:
a data transfer module, which is coupled to the processing module and signally connected to a remote server.

5. The system according to claim 4, wherein the remote server reads the data of the two-dimensional barcodes, and returns the processing module through the data transfer module to assist the person to take medicine.

6. The system according to claim 4, wherein the remote server has a data storage module which stores barcode data.

7. The system according to claim 6, wherein the remote server receives read data, outputted from the processing module according to the data of the two-dimensional barcodes, compares the read data with the barcode data of the data storage module, and converts the read data into assistance medication data returned to the processing module.

8. The system according to claim 1, wherein the two-dimensional barcodes are disposed on the pill container before or after the pill container contains the medicine by way of printing, adhering or engraving.

9. A method for assisting a person to take medicine, the method comprising the steps of:
containing medicine in a plurality of pill containers detachably disposed in the housing units of an electronic medicine box respectively, wherein the electronic medicine box comprises a base and a plurality of upper cover portions, the base has a plurality of housing units, the portions movably are respectively connected to the housing units, and a plurality of positioning patterns are disposed on the electronic medicine box, wherein each of the pill containers comprises an accommodating portion and a cover portion, the accommodating portion is configured to contain a medicine, the cover portion is configured to be movably connected to the accommodating portion and to have a two-dimensional barcode corresponding to the medicine in the accommodating portion, wherein when the pill containers are disposed in the electronic medicine box, the two-dimensional barcodes are readable;
capturing an image, having the two-dimensional barcodes and the positioning patterns, through an image capturing module;
generating a boundary of each of the positioning patterns through a processing module;
marking four corners of the boundary of each of the positioning patterns through the processing module;
connecting an innermost corner of each of the positioning patterns to define a reading area through the processing module;
dividing the reading area into a plurality of reading blocks, each of the two-dimensional barcodes being positioned in one of the reading blockings respectively through the processing module;
reading the two-dimensional barcodes in the reading blocks respectively through the processing module; and
outputting an assisting signal to assist a person to take medicine according to the data of the two-dimensional barcode through the processing module,
wherein the electronic medicine box or a handheld electronic device controls the pill container to open at a time point or to output a reminding signal at a time point according to the assisting signal.

10. The method according to claim 9, wherein the processing module is disposed in the electronic medicine box or the handheld electronic device.

11. The method according to claim 9, wherein at least two of the pill containers contain different medicine.

12. The method according to claim 9, wherein the processing module is coupled to a data transfer module, which is signally connected to a remote server.

13. The method according to claim 12, wherein the remote server reads the data of the two-dimensional barcodes, and returns the processing module through the data transfer module to assist the person to take medicine.

14. The method according to claim 12, wherein the remote server has a data storage module which stores barcode data.

15. The method according to claim 14, wherein in the step of assisting the person to take medicine, the remote server receives read data, outputted from the processing module according to the data of the two-dimensional barcodes, compares the read data, with the barcode data of the data storage module, and converts the read data into assistance medication data returned to the processing module.

16. The method according to claim 9, wherein the two-dimensional barcodes are disposed on the pill container before or after the pill container contains the medicine by way of printing, adhering or engraving.

* * * * *